United States Patent [19]

McLaughlin et al.

[11] Patent Number: 5,413,783
[45] Date of Patent: May 9, 1995

[54] INHIBITING PLANT PATHOGENS WITH AN ANTAGONISTIC MICROORGANISM(S)

[75] Inventors: Randy J. McLaughlin, Martinsburg, W. Va.; Charles L. Wilson, Frederick, Md.; Edo Chalutz, Rishon le 'Zion, Israel

[73] Assignee: The United States of America as represented by the Secretary of Agriculture, Washington, D.C.

[21] Appl. No.: 395,681

[22] Filed: Aug. 18, 1989

Related U.S. Application Data

[63] Continuation-in-part of Ser. No. 387,669, Jul. 31, 1989, abandoned, and a continuation-in-part of Ser. No. 177,236, Apr. 4, 1988, abandoned.

[51] Int. Cl.$^6$ .................. C12N 1/16; A01N 63/00
[52] U.S. Cl. .................. 424/93.51; 424/93.1; 424/93.3; 424/93.4; 424/93.5; 435/255.1; 435/55.5; 435/255.6; 435/938
[58] Field of Search .................. 424/93 R, 938, 93 C, 424/93 D, 93 Q, 93 S; 435/255, 255.5, 255.6, 255.1

[56] References Cited

U.S. PATENT DOCUMENTS

| | | | |
|---|---|---|---|
| 4,686,187 | 8/1987 | Sakai et al. | 435/275 |
| 4,764,371 | 8/1988 | Pusey et al. | 435/839 |
| 4,877,738 | 10/1989 | Handelsman et al. | 435/254 |
| 4,886,664 | 12/1989 | Jung et al. | 435/254 |
| 5,041,384 | 8/1991 | Wilson et al. | 435/938 |
| 5,049,379 | 9/1991 | Handelsman et al. | 435/839 |
| 5,068,105 | 11/1991 | Lewis et al. | 424/93 R |
| 5,192,541 | 3/1993 | Spuage | 424/93 D |
| 5,194,258 | 3/1993 | Paau et al. | 424/93 Q |

FOREIGN PATENT DOCUMENTS 0286351 12/1988 European Pat. Off.
9010388 9/1990 WIPO ................ 435/932

OTHER PUBLICATIONS

Conway, W. S. et al, 1983, Phytopathology, vol. 73, No. 7:1068.

Stollarova, Viera, 1982, Biologia (Bratislava), 37, 11, 1115–1120.

Kamra, Neelam et al, 1987, Microbios Letters, 34, 79–85.

Chalutz, E., Droby, S., Wilson, C. L., 1988, Mechanisms of action of postharvest biocontrol agents, 5th Int. Congr. of Plant Path., p. 422, Kyoto, Japan (Abstract).

McLaughlin, R. J. et al, "Biocontrol of Postharvest Rots . . . " (abstract) Am. Phyto. Society Annual Meeting Aug. 19, 1989.

Wisniewski, M. et al, "Biological Control of Postharvest Diseases of Fruit . . . " Proceedings of the 46th Ann Meeting of the Elec. Mic. Soc. of Am., pp. 290–291, Aug. 7, 1988.

Chalutz, E. et al, "Microbial Protection Against Postharvest Disease of Citrus Fruit", Phytoparasitica, 16:2, 1988 (195–196).

Chalutz, E. et al, "Yeasts as Biocontrol Agents of Postharvest Diseases of Fruits", Phytoparasitica, 16:1, 1988 (69).

"Common Yeast Strongly Inhibits Undesirable Fungi on Stored Citrus 4405" in European Biotechnology Newsletter, published Mar. 25, 1988.

"Biological Control of Postharvest Diseases of Fruit and Vegetables . . . ", Wilson et al, Annv. Ref. Phytopathol., Sep. 1, 1989:27:425–441.

"Postharvest Biological Control of Penicillium Rots of Citrus with Antagonistic Yeast and Bacteria" by Charles L. Wilson et al, Scienta Horticultural, vol. 40(2), Aug. 9, 1989.

(List continued on next page.)

*Primary Examiner*—Herbert J. Lilling
*Attorney, Agent, or Firm*—Janelle S. Graeter; M. Howard Silverstein; John D. Fado

[57] ABSTRACT

The present invention is drawn to biological control of plant pathogens (e.g. either preharvest or postharvest diseases) on agricultural commodities (such as fruits, vegetables, cereals, grains, nuts, seeds and silage) by use of at least one microorganism which is an antagonist against plant pathogens.

18 Claims, 8 Drawing Sheets

OTHER PUBLICATIONS

Derwent Abs., 81-134996, J56134996 (Oct., 1981), Nagai et al.
Chem. Abs. 95-146874(17), Hobot et al, Exp. Mycol, vol. 5(3), pp. 217-228 (1981).
Chem. Abs., 84-149427(21), Yamauchi et al, NICKA3, vol. 47(1), pp. 12-17, (1976).
Pusey, P. L. et al, "Postharvest Biological Control of Stone Fruit Brown Rot . . . ", Plant Disease 68(9), 753-756 (1984).
Singh, V. et al, "Bacillus Subtilis as a Control Agent Against Fungal Pathogens . . . ", Trans. Br. Mycol. Soc. 83:487-490(1983).
Wilson, C. L. et al, "Potential for Biological Control of Postharvest Plant Disease", *Plant Disease* 69:375-378(1985).
A. P. de Matos, "Chemical and Microbiological Factors Influencing the Infection of Lemons by *Geotrichum candidum* and *Pencillium digitatum*", Ph. D. Dissentation, Univ. of Calif., Riverside (1983).
The Condensed Chemical Dictionary, 10th Edition, Gessner G. Hawley, 1981, p. 180, Van Nostrand Reinhold Co., N.Y.
Janisiewicz, W. J., 1987, Phytopathology, vol. 77, No. 3:481.
Janisiewicz, W. J., 1988, Phytopathology, vol. 78, No. 2:194.
E. Chalutz et al, "Biocontrol of Postharvest Diseases of Citrus Fruits . . . " abstract handed out to theparticipants of the International Citrus Congress-Middle East, Tel Aviv, Israel, Mar. 6-11, 1988.
E. Chalutz et al, "Microbial Protection Against Postharvest . . . " abstract handed out to the participants of the Bat-Sheva Seminar on Host-Fungus Interaction, Jerusalem, Israel, Mar. 14-25, 1988.
McLaughlin, R. J. et al, "Characterization and Reclassification of Yeasts Used for Biological Control . . . ", Applied and Environmental Microbiology, vol. 56, No. 11, Nov. 1990, pp. 3583-3586.
Chem. Abs. 71-110097-(23) Merginger et al, Appl. Microbio., vol. 18(3), pp. 365-368, (1969).
Chem. Abs. 10-6447(1), Gardini et al, LBWTAP, vol. 21(3), pp. 137-143, 1988.
Wilson, C. L. et al, 1987, Phytopathology, vol. 77, No. 2:303.
Janisiewicz, W. J. et al, 1988, Phytopathology, vol. 78, No. 2:1697.
Conway, W. S., 1982, Plant Disease, vol. 66, No. 5:402.
Wisniewski, M. et al, "Biological Control of Postharvest Diseases of Fruit . . . " Pro . of the 46th Annual Meeting of the Electron Microscopy Society of America, pp. 290-291, Aug. 7, 1988.
Gardini, F. et al, "$CO_2$ Determination with the GC Method for Assessing . . . ", Lebensm.-Wiss. U.-Technol., 21, 137-143 (1988).
Derwent Abstract 81-89777P/49, Asahi Chemical, J56134996-A (Oct. 1981).

INHIBITING PLANT PATHOGENS WITH AN ANTAGONISTIC MICROORGANISM(S)

CROSS-REFERENCE TO RELATED APPLICATIONS

The present application is a continuation-in-part of application Ser. No. 07/387,669 filed Jul. 31, 1989 entitled "Inhibiting Plant Pathogens with Nonantibiotic Antagonistic Microorganism(s)" by Charles L. Wilson and Edo Chalutz, and now abandoned, and a continuation-in-part of application Ser. No. 07/177,236 filed Apr. 4, 1988, and now abandoned.

BACKGROUND OF THE INVENTION

1. Field of the Invention

The present invention relates to the biological control of plant diseases (e.g. either pre-harvest or postharvest diseases) in agricultural commodities such as fruit. More particularly, this invention relates to: (1) methods for biologically controlling plant diseases (such as post harvest rots) on agricultural commodities using either, (a) at least one calcium salt and at least one microorganism which is an antagonist to plant pathogens, or (b) at least one microorganism which is an antagonist against plant pathogens but is not antibiotic; (2) compositions useful in such methods, and; (3) manufactures produced by such methods.

2. Description of Prior Art

Postharvest diseases of fruit cause 15 to 25% losses yearly in the fruit industry worldwide. Fungicides, the major weapon in combatting these diseases, are often ineffective and pose hazards to humans and the environment. Therefore, a critical need exists for new methods to control postharvest diseases without posing such hazards to humans or the environment.

Recently, it has been shown that the postharvest treatment of fruit with antagonistic microorganisms is an effective approach to the control of postharvest rots. Remarkable success was shown in the control of brown rot in peaches caused by *Monilinia fructicola* (Wint.) Honey with *Bacillus subtilis*. Pusey et al. [Plant Dis. 86:753–756 (1986)]. De Matoswas able to reduce mold incidence from 35% to 8% when a species of Trichoderma was inoculated with *Penicillium digitatum* into lemon peel. De Matos, Ph.D. Dissertation, University of California, Riverdale, (1983). Singh and Deverall demonstrated biocontrol with bacterial antagonists to the citrus pathogens *Alternaria citri* Pierce, *Geotrichum candidum* link. ex Pers., and *P. digitatum*. Singh et al. [Trans. Br. Mycol. Soc. 83:487–490 (1983)]. Dipping wounded citrus fruit in suspensions of bacterial cells, particularly a strain of *Bacillus subtilis* (Ehrenber) Cohn, delayed decay by the three rot pathogens.

SUMMARY OF THE INVENTION

A first aspect of the present invention relates to processes for inhibiting plant pathogen development on an agricultural commodity comprising: applying (in the context of the present invention, "applying" is intended to be limited to the intentional and willful dispensing of the microorganism(s) onto the agricultural commodity, as opposed to the natural occurrence of a microorganism on an agricultural commodity) to an agricultural commodity at least one microorganism, the at least one microorganism being an antagonist against plant pathogens but not being antibiotic, wherein the at least one microorganism is applied in an amount effective to inhibit plant pathogen development on the agricultural commodity. The most striking and novel aspect of this invention is the use of microorganisms which do not produce antibiotics to control the diseases of agricultural commodities. This method is of importance to the consumer because it avoids the potential adverse effects of antibiotics in the food supply, such as the development of antibiotic resistance in human pathogens.

A second aspect of the present invention relates to processes for inhibiting plant pathogen development on an agricultural commodity comprising: applying to the agricultural commodity at least one calcium salt and at least one microorganism which is an antagonist against plant pathogens (and preferably not antibiotic); wherein the at least one calcium salt and the at least one microorganism are applied to the agricultural commodity in an amount effective to inhibit plant pathogen development on said agricultural commodity.

A third aspect of the instant invention pertains to compositions which may be utilized in carrying out the aforementioned processes. Such compositions include:

A composition comprising a mixture of, (1) at least one microorganism which is an antagonist against plant pathogens but is not antibiotic and, (2) a carrier for said at least one microorganism selected from the group consisting of a gel, gum, wax, oil, talc, starch and mixtures thereof;

A composition comprising a mixture of, at least one microorganism and a carrier for said at least one microorganism, wherein at least 99% by count of said at least one microorganism is antagonistic against plant pathogens but is not antibiotic; and/or, A composition comprising a mixture of, at least one calcium salt and at least one microorganism which is an antagonist against plant pathogens, and preferably is not antibiotic (preferably such a composition may: (a) consist essentially of the at least one calcium salt and the at least one microorganism, and/or; (b) have at least 99% by count of microorganisms therein be antagonistic to plant pathogens, and/or; (c) have at least 99% by count of microorganisms therein be nonantibiotic).

A fourth aspect of the present invention relates to manufactures which may include:

A manufacture comprising an agricultural commodity having thereon a concentration of at least about $10^5$ colony forming units per square centimeter of at least one microorganism which is an antagonist against plant pathogens but is not antibiotic;

A manufacture comprising an agricultural commodity having microorganisms thereon, wherein the majority of said microorganisms are at least one microorganism which is an antagonist against plant pathogens but is not antibiotic;

A manufacture comprising an agricultural commodity having thereon a calcium salt and at least one microorganism which is an antagonist against plant pathogens (and preferably is not antibiotic) in a concentration of at least about $10^5$ colony forming units per square centimeter; and/or A manufacture comprising an agricultural commodity having a calcium salt and microorganisms thereon, wherein the majority of microorganisms on said agricultural commodity are at least one microorganism which is an antagonist against plant pathogens.

A fifth aspect of the present invention relates to a biologically pure culture of an isolate of *Hanseniaspora*

*uvarum* having the identifying characteristics of isolate NRRL Y-18527.

The aforementioned microorganism(s) may for example be selected from the group consisting of: fungi (e.g. yeast), bacteria, viruses and mixtures thereof.

In regard to a preferred embodiment of the present invention, we have discovered new strains of yeast that are highly effective in controlling a variety of plant (e.g. fruit-rot) pathogens which affect a wide variety of agricultural commodities. Three isolates of the new strains have been deposited with the culture collection at The Northern Regional Research Center, U.S. Department of Agriculture, Peoria, Ill. 61604, under the acquisition numbers NRRL Y-18313, NRRL Y-18314 and NRRL Y-18527. NRRL Y-18314 has been identified as *Pichia quilliermondii* and NRRL Y-18527 has been identified as *Hanseniaspora uvarum* (Nichaus) Shehata, Mrak et Phaff. The deposited materials have been accepted for deposit under the Budapest Treaty on the International Recognition of the Deposit of Microorganisms for the purposes of patent procedure. Further, (1) said depository affords permanence of the deposits and ready accessibility thereto by the public if a patent is granted, (2) the materials have been deposited under conditions that assure that access to the materials will be available during the pendency of the patent application to one determined by the Commissioner of Patents and Trademarks to be entitled thereto under 37 CFR 1.14 and 35 USC 122. All restrictions on the availability of progenies of the strain to the public will be irrevocably removed upon the granting of the patent.

Accordingly, it is an object of the present invention to provide novel biological control agents which pose no risk to the consumer and are highly effective in controlling a variety of plant pathogens causing preharvest and postharvest diseases on a variety of agricultural commodities (e.g. fruits).

It is also an object of the invention to provide a method of biologically controlling plant diseases (e.g. postharvest diseases) on agricultural commodities (e.g. fruits) which does not require the use of fungicidal treatments.

In a preferred embodiment of our invention, agricultural commodities are subjected to an aqueous suspension comprising an isolate of yeast having the identifying characteristics of an isolate selected from the group consisting of: NRRL Y-18313, NRRL Y-18314, NRRL Y-18527 and mixtures thereof. In effect, the organisms multiply and occupy the surfaces of wounded fruit, thereby preventing infection by plant (e.g. fruit-rot) pathogens.

The file of this patent contains at least one drawing executed in color. Copies of this patent with color drawing(s) will be provided by the Patent and Trademark Office upon request and payment of the necessary fee.

DESCRIPTION OF THE PREFERRED EMBODIMENTS

Figure 1:
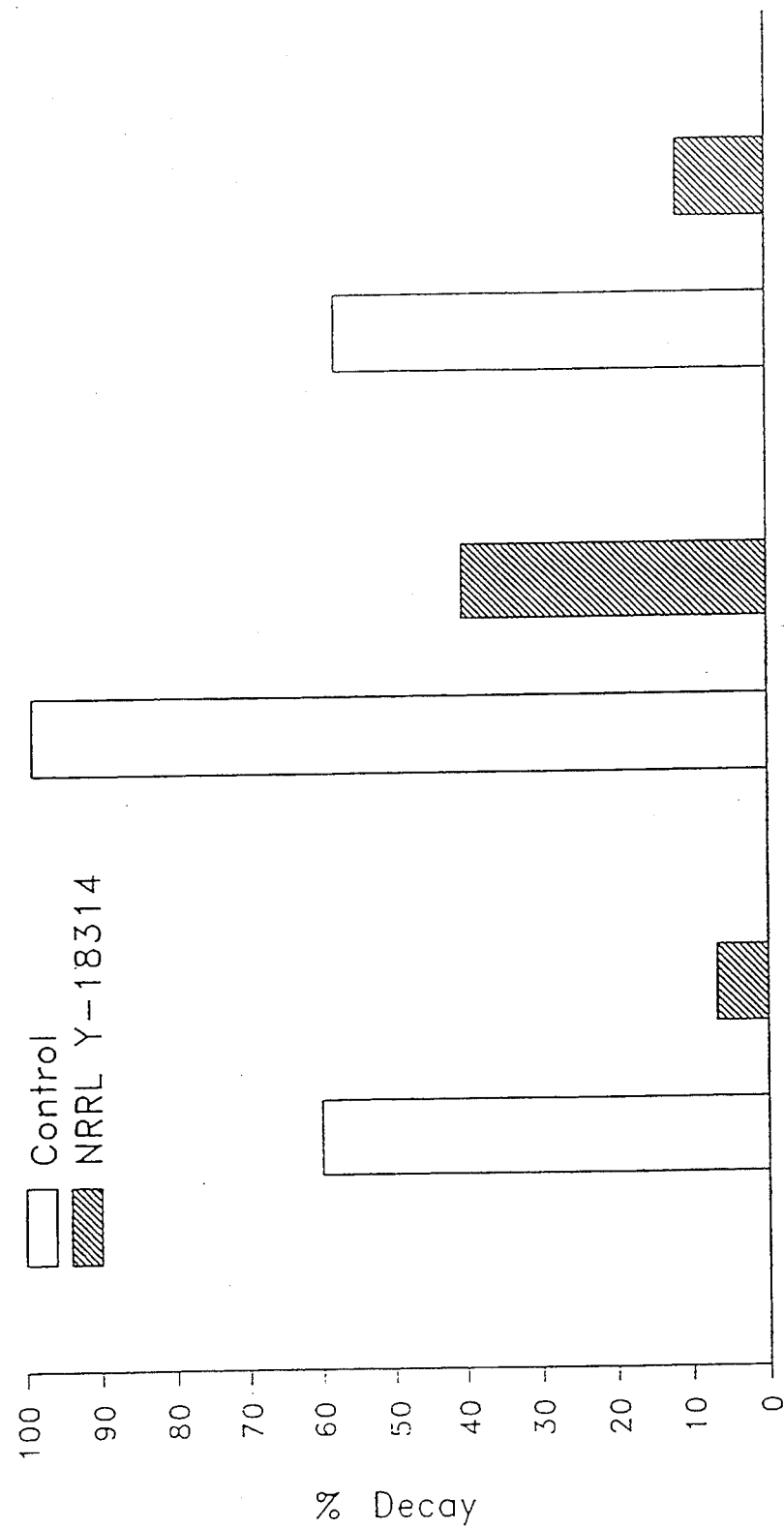
FIG. 1 is a bar graph of percent decay of grapes treated with NRRL Y-18314 and grapes in a control group, showing inhibition of Rhizopus rot.

Aspects of the present invention my be practiced with a variety of microorganisms which are antagonistic against plant pathogens (such microorganisms my for example exert their antagonism by either out competing the pathogen for available nutrients or rendering the infection site unfavorable for the pathogen) but which are not antibiotic, including: fungi (e.g. yeasts, for example, at least one yeast selected from the group consisting of yeasts having the identifying characteristics of deposite NRRL Y-18313, NRRL Y-18314, and NRRL Y-18527) bacteria, viruses and mixtures thereof.

Microorganisms useable in the present invention my for example be identified by the following procedure:

(1) screening agricultural commodities (e.g. the surface(s) of said agricultural commodities) for the presence of a microorganism(s);

(2) recovering (e.g. by washing or rinsing from the agricultural commodity) and isolating said microorganism(s);

(3) testing said microorganism(s) for antagonistic activity against plant pathogens, and;

(4) in regard to those aspects of the instant invention relating to nonantibiotic microorganisms, testing for absence of antibiotic activity. However, it should be understood that said microorganism(s) may be obtained from sources other than said agricultural commodities.

In regard to a preferred embodiment of the present invention, isolates of NRRL-Y-18313 and NRRL-Y-18314 were obtained from the surface of citrus fruits by repeatedly washing the fruit with water, and NRRL Y-18527 was isolated from the surface of a grape. NRRL Y-18527 has been identified as Hanseniaspora uvarum (Nichaus) Shehata, Mrak et Phaff. The organisms are thereafter plated and grown on any nutritionally rich medium sufficient to support growth of the organisms. Preferably, the medium is either nutrient yeast dextrose agar (NYDA) or yeast-malt extract agar (YM).

Isolates NRRL-Y-18313 and NRRL-Y-18314 have the following identifying characteristics as determined by the American Type Culture Collection: colonies are cream white, slightly raised, shiny, round and smooth. No pseudohyphae were observed. No ascospores were produced after one week on Corn Meal agar, V-8 Juice agar, YM or acetate. On solid YM, cells are unicellular in liquid culture after one day. Small globose cells are observed mainly in chains or clusters, many with one bud.

Isolate NRRL Y-18527 has the following identifying characteristics as determined by the American Type Culture Collection: in liquid medium, cells appear lemon shaped and have bipolar budding. On solid medium, cells remain unicellular or non-filamentous. Colonies are white, dull with a slightly raised surface. Pseudomycelium is not produced. One round ascospore is produced per cell.

Biochemical and physiological tests of the isolates were as follows:

| Carbon Assimilation: | NRRL-Y-18314 | NRRL-Y-18313 | NRRL-Y-18527 |
|---|---|---|---|
| Glucose | + | + | + |
| Galactose | + | + | − |
| L-sorbose | + | + | − |
| Maltose | + | + | − |
| Sucrose | + | + | − |
| Cellobiose | + | + | + |
| Trehalose | + | + | − |
| Lactose | − | − | − |
| Melibiose | + | − | − |
| Raffinose | + | + | − |
| Melezitose | + | + | − |
| Inulin | + | + | − |
| Soluble Starch | w | w | NT* |
| D-xylose | + | + | − |
| L-arabinose | + | + | − |
| D-arabinose | + | + | − |
| D-ribose | + | + | NT |
| L-rhamnose | + | w | − |
| D-glucosamine | + | w | NT |
| Ethanol | w | w | − |
| Erythritol | w | − | NT |
| Glycerol | + | + | − |
| Adonitol (Ribitol) | + | + | − |
| Dulcitol (Galactitol) | + | + | − |
| D-mannitol | + | + | NT |
| D-sorbitol (glucitol) | + | + | − |
| a-methly-D-glucoside | + | + | − |
| Salicin | + | + | + |
| Inositol | − | − | NT |
| Lactic acid | w | + | NT |
| Citric acid | + | + | NT |
| Succinic acid | + | + | NT |
| Nitrogen assimilation: | NRRL-Y-18314 | NRRL-Y-18313 | NRRL-Y-18527 |
| $NH-NO_3$ | + | + | + |
| $KNO_3$ | + | + | + |
| $NO_2$ | w | w | NT |
| Ethylamine | + | + | + |
| Fermentation: | NRRL-Y-18314 | NRRL-Y-18313 | |
| Glucose | + | + | + |
| Galactose | w | + | − |
| Maltose | − | − | − |
| Sucrose | + | + | − |
| Lactose | − | − | − |
| Raffinose | − | − | − |
| Melibiose | − | − | − |
| Inulin | w | − | − |
| Cellobiose | − | − | + |
| Melezitose | − | − | − |
| Starch | − | − | − |
| Trehalose | − | − | + | w = weak
NT = not tested

Growth of isolates NRRL Y-18313 and NRRL Y-18314 may be effected under aerobic conditions at any temperature satisfactory for growth of the organisms, i.e. from about 10° C. to about 30° C. The preferred temperature range is about 20° C. to 25° C. The pH of the nutrient medium is about neutral, i.e. 6.7 to 7.2. The incubation time is that time necessary for the isolates to reach a stationary phase of growth, preferably, from about 40 to 60 hours. Growth of isolate NRRL Y-18527 is preferably achieved at a temperature range of 25°–28° C. with an incubation time of 18 to 24 hours, such that cells are in the logrithmic phase of growth.

Isolates NRRL-Y-18313, NRRL-Y-18314 and NRRL Y-18527 may be grown in any conventional shake flask for small fermentation runs. For large scale operations, it is convenient to carry out the culture in a fermentation tank, while applying agitation and aeration to the inoculated liquid medium. Following incubation, the isolates are harvested by conventional sedimentary methodology (e.g. centrifugation) or filtering. Cultures are stored on silica gel and frozen at −20° C. until use.

The microorganisms of the present invention (including isolates NRRL-Y-18313, NRRL-Y-18314, and/or NRRL Y-18527) are useful to control a variety of plant pathogens. Exemplary species of plant pathogens include, but are not limited to, Penicillium italicum Wehmer, Penicillium digitatum, Botrytis cinerea, Rhizopus stolonifer, Geotrichum candidum, Penicillium expand, Alternaria alternata, Aspergillus flavus, Aspergillus niger, Rhizopus arrhizus, Gilbertella persicovia, Mucov spp., Pezicula malicorticas, Monilinia spp. (e.g. Monilinia fructicola or Monilinia laxa), and bacterial pathogens.

The microorganisms of the invention are useful in controlling plant pathogens on a variety of agricultural commodities including, but not limited to: fruits, vegetables (e.g. celery), cereals, grains, nuts, seeds, and silage. Examples of fruits with which the present invention may be carried out include but are not limited to, citrus fruit, grapes, apples, pears, tomatoes, persimmons, strawberries, peaches, apricots, cherries and papayas. Said citrus fruit may for example include: grapefruit, orange, lemon, kumquat, lime and pummelo. Said nuts may for example include: peanuts, almonds and pecans. Said grains may for example include: wheat, corn, sorghum, soybean and barley. The microorganisms of the present invention may also be utilized with processed agricultural commodities including for example, raisins, prunes, figs, dried apricots and dates.

The microorganisms of the present invention may be applied to agricultural commodities in combination with a variety of additives, including carriers such as: (1) a gel or gum based carrier (e.g. xanthan gum); (2) a water based carrier (e.g. the microorganisms may be mixed/suspended in water. Other water based carriers include water plus wetting and/or spreading agents); (3) an oil based carrier (e.g. "Fresh Mark" or "Fresh Wax 58P" (which is a paste wax for peaches, plums and nectarines, containing—white oil, paraffin, wax, petrolatum and oleic acid) both from Fresh Mark Chemical Corporation, Orlando, FL); (4) a wax based carrier (e.g. including wax coatings typically used on citrus fruit and apples, for example "Britex 551" or "Britex 559", both from Broshar (Chemicals) Ltd., Kefar-Saba, Israel); (5) a powdered carrier ingredient to provide the composition in powdered form, and in which the microorganism(s) are dispersed and thus diluted to a desired concentration in the powdered composition (examples of such powdered carrier ingredients are: starch (e.g. corn starch) and/or talc), and; (6) and mixture of the foregoing. Use with oil based carriers is preferred to use with water based carriers because the antagonist typically survives better in an oil based carrier. When grown in a liquid medium, the microorganisms may be applied in suspension with the liquid medium, however it is preferred in order to improve control, to apply the microorganisms in the presence of water or one or more of the aforementioned carriers. Compositions of the present invention may also include other additives including: (1) pesticides, such as fungicides (e.g. "TBZ" available from FMC Corporation); (2) one or more preservatives i.e. an environment enhancer such as compositions which hold moisture and/or help to maintain the microorganism(s) viable during storage and/or use, including e.g.: (a) a gum, for example a natural gum, such as guar gum, locust bean gum, karaya gum, tragacanth gum or preferably xanthan gum; (b) methyl cellulose; (c) silica gel, and; (d) mixtures of the foregoing preservatives; (3) surfactants and wetting agents, such as Tween 20 and Triton X-100 available from Rhom and Hass Company; (4) additives which promote spreading of the compositions oft he present invention; (5) additives which promote sticking of the compositions of the present invention to agricultural commodities; (6) nutrients for the microorganisms of the present invention, and; (7) mixtures of the aforementioned additives. When used, these additives should be used in an amount(s) which will not interfere with the effectiveness of the microorganism(s) of the present invention. Typically, preparation of suitable compositions require only mixing of the microorganism(s) with the additives. Typical preparation includes, adding together the microorganism(s), preservative and powdered ingredient, and then mixing and/or grinding the constituents together. The powdered composition may be dusted on an agricultural commodity, or the powdered composition may be mixed with liquid (e.g. water) and subsequently applied to an agricultural commodity. The compositions of the present invention have excellent storage properties, do not require refrigeration, do not typically encounter contamination problems, and remain effective in typical fruit, vegetable and grain storage environments.

When the compositions of the present invention are in the form of a liquid mixture or suspension, any concentration of constituents may be used which inhibits plant pathogen development of the targeted plant pathogen when applied to an agricultural commodity. As will be apparent to one skilled in the art, effective concentrations may vary depending upon such factors as: (1) the type of agricultural commodity; (2) the physiological condition of the agricultural commodity (e.g. ripeness ); (3) the concentration of pathogens affecting the agricultural commodity; (4) the type of wound on the agricultural commodity; (5) temperature and humidity; and (6) the age of the plant pathogen. Exemplary concentrations range from about $1\times10^4$ to $1\times10^9$ CFU/ml, most preferably, from about $1\times10^7$ to $1\times10^9$ CFU/ml. For purposes of this invention, the abbreviation "CFU" is used herein to designate "colony forming units." According to one aspect of the present invention the microorganism(s) are applied to the agricultural commodity in a preparation which is essentially free of other microorganisms.

The microorganisms of the invention may be applied to agricultural commodities using conventional methods such as dusting, injecting, rubbing, rolling, dipping, spraying or brushing. In addition, the microorganisms of the invention may be incorporated into a variety of compositions suitable for application to agricultural commodities, including waxes, wraps or other protective coatings used in processing the agricultural commodity.

The natural or normal concentration of isolates NRRLY-18313, NRRLY-18314, and NRRLY-18527 on fruit may typically vary from 0 to 100 CFU/$cm^2$. *Hanseniaspora uvarum,* or its asexual form *Kloeckera apiculata,* is commonly found as a natural component of the microbial flora that inhabit fruit surfaces (Kamra N., and Madan, M., 1987, Microbios. Lett. 34:79; Stollarova, V., 1982, Biologica (Bratsil) 37:1115–1121). However, the ability of these yeasts to control plant pathogens was unexpected since these yeast species have not previously been reported to have biological control properties. One aspect of the present invention relates to applying the microorganism(s) of the present invention in concentrations significantly greater than the aforementioned natural/normal concentrations, e.g. at least about $10^5$ CFU per $cm^2$, or preferably at least about $10^6$ CFU per $cm^2$. It should be noted in this regard, that another aspect of the present invention relates to an agricultural commodity having thereon a calcium salt and at least one antagonistic microorganism of the present invention in a concentration of at least about $10^5$ CFU/$cm^2$.

The agricultural commodities maybe treated any time before or after harvest. Typically, the preferred time of treatment is after harvest and prior to storage or shipment. In the case of some grapes, the preferred time of treatment is before harvest.

It is within the scope of the present invention to treat the agricultural commodity with isolates NRRL-Y-18313, NRRL-Y-18314 or NRRLY-18527 alone, or in combination.

It has surprisingly and unexpectedly been discovered that use of at least one calcium salt with the at least one microorganism of the present invention facilitates improved control of plant pathogens (notably, *Rhizopus stolonifer* of peaches, major rot pathogens of table grapes, Penicillium and Botrytis rot of apples and Penicillium rot of grapefruit). The enhanced ability of the microorganism(s) of the present invention to control plant pathogens in the presence of at least one calcium salt is especially unexpected in view of the fact that topical treatment of fruit with calcium chloride was shown not to reduce postharvest rot of apply by Conway; 1981-Plant Disease 66:402–403 and, Conway et al 1983 Phytopathology 73:1068–1011. While not wishing to be bound by a theory, Applicants believe that the dramatic effect of the calcium salt(s) on biocontrol may be the result of calcium cation interaction with the microorganism(s), perhaps by affecting the antagonistic microorganisms survival at the wound site or by affecting its metabolism or by interaction with its metabolic products. In regard to preferred embodiments of the present invention relating to use of calcium chloride, it is especially surprising and unexpected that: calcium chloride applied as a topical treatment would be useful as an agent for enhancing biological control of plant pathogens; calcium chloride would be Fore effective for enhancing biocontrol than other salts containing similar cations and anions, and; the effects of calcium chloride would be, exerted against such a wide variety of plant pathogens and, manifested with such a broad variety of biocontrol agents. The at least one calcium salt and at least one microorganism may be applied to the agricultural commodity separately, or for ease of application may be applied as a mixture (e.g. also containing one or more of the aforementioned additives). Typical examples of the calcium salt include: calcium chloride, calcium carbonate, calcium propionate, and mixtures thereof. For example, calcium chloride may be utilized in concentrations of about 1 gm/100 ml to about 10 gm/100 ml, preferably about 1 gm/100 ml to about 5 gin/100 ml, and most preferably about 2 gm/100 ml.

The following examples are intended to further illustrate the invention and not to limit the scope of the invention as defined by the claims.

EXAMPLE 1

The effectiveness of yeast NRRL-Y-18314 was evaluated using the following seven citrus cultivars: grapefruit (*Citrus paradisi* Macf. cv 'Marsh Seedless'); 'Shamouti' and 'Valencia' orange (*C. sinensis* Osbeck); lemon (*C. lemon* L. Burm 'Eureka'); Temple orange (Tanger hybrid, *C. reticulata* X *C. sinensis*); Kumquat (*Fortunella margarita*); and pummelos, (*C. grandis*). Fruit rot pathogens tested included *Penicillium digitatum, Penicillium italicum* and *Geotrichum candidurn* Link. ex Pers., fungi responsible for the postharvest diseases green-mold, blue-mold and sour-rot, respectively.

A biologically pure culture of isolate NRRL-Y-18314 was obtained using the following procedures: The surface of lemons was washed by placing the fruit in a 600 ml beaker containing 200 ml of sterile water. The beakers containing the fruit were placed on a rotary shaker at 100 rpm for 10 minutes. One tenth ml of the wash water was then spread on a NYDA plate and allowed to incubate for 24 hours before colonies were selected. The same fruit received three separate washings and the same procedures were followed. Appearing colonies were isolated and purified using standard purification techniques. All cultures were stored on silica gel in a freezer until use.

Isolate NRRL-Y-18314 was grown in flasks containing nutrient yeast dextrose broth (NYDB) on a reciprocal shaker at 30° C. for 48 hours. The culture was centrifuged at 7000 rpm for 10 minutes and the resulting pellet was suspended in water at various concentrations. Concentrations of the aqueous suspensions were adjusted on a spectrophotometer.

Freshly harvested fruit was wiped with 95% ethanol and placed on moist paper in 50×100×15 cm plastic trays, 24 fruits per tray. Two to four conical wounds, 3 mm deep, were cut in the fruit peel. The wounds were brushed with an aqueous suspension of NRRL Y-18314. The concentration of the aqueous suspension was $1 \times 10^9$ CFU/ml. One to two hours later, 20 microliters of an aqueous spore suspension of the targeted pathogen, $1 \times 10^4$ spores/ml, were pipetted into the wounds. Control fruits were inoculated with aqueous spore suspensions of the targeted pathogen only. Following incubation, the trays were covered with high density polyethylene sleeves and kept at room temperature for several days.

The number of inoculated sites on which decay developed was determined daily. Each treatment in each experiment consisted of at least 3 replicates of 6 fruits, 24 to 75 inoculation sites per treatment. Each experiment was repeated at least twice.

Results were analyzed and are recorded in Tables I, II, and III below.

TABLE I

Relative effectiveness of NRRL Y-18314 in inhibiting *Penicillium digitatum* decay of different citrus cultivars.

| Citrus cuitivar | Antagonist | Incubation time (days) | | | |
|---|---|---|---|---|---|
| | | 4 | 5 | 6 | 7 |
| | | Percent Infection[a] | | | |
| Grapefruit | NRRL Y-18314 | 0 | 2 | 6 | 11 |
| (72) | Control | 90 | 97 | 100 | 100 |
| Orange, 'Shamouti' | NRRL Y-18314 | 0 | 3 | 10 | 17 |
| (42) | Control | 93 | 100 | 100 | 100 |
| Orange, 'Valencia' | NRRL Y-18314 | 2 | 4 | 8 | 17 |
| (42) | Control | 90 | 94 | 97 | 100 |
| Lemon | NRRL Y-18314 | 0 | 2 | 10 | 15 |
| (42) | Control | 98 | 100 | 100 | 100 |
| Temple | NRRL Y-18314 | 2 | 4 | 10 | 14 |
| (48) | Control | 95 | 96 | 99 | 100 |
| Pummelo | NRRL Y-18314 | 0 | 0 | 2 | 2 |
| (24) | Control | 83 | 90 | 92 | 96 |
| Kumquat[b] | NRRL Y-18314 | 4 | 8 | 12 | — |
| (150) | Control | 19 | 23 | 37 | — |

[a]Number of inoculation sites per treatment is indicated in parentheses under the cultivar's name.
[b]Whole fruits were used without artificial inoculation. The fruit was dipped momentarily in a 48 hr-old liquid culture of the NRRL Y-18314. NYDB was used as control.

TABLE II

Inhibition of *Penicillium italicum* decay of grapefruit and orange by NRRL Y-18314

| Citrus cultivar | Antagonist | Incubation time (days) | | | |
|---|---|---|---|---|---|
| | | 3 | 4 | 5 | 6 |
| | | Percent Infection[a] | | | |
| Grapefruit | NRRL Y-18314 | 3 | 3 | 4 | 6 |
| (72) | Control | 97 | 100 | 100 | 100 |
| Orange 'Valencia' | NRRL Y-18314 | 3 | 8 | 10 | 19 |
| (72) | Control | 84 | 95 | 97 | 100 |
| Orange 'Shamouti' | NRRL Y-18314 | 3 | 6 | 8 | 15 |
| (72) | Control | 90 | 95 | 100 | 100 |

[a]Number of inoculation sites per treatment is indicated in parentheses under the cultivar's name.

TABLE III

Inhibition of *Geotrichum candidum* decay of grapefruit and lemon by NRRL Y-18314

| Citrus cultivar | Antagonist | Incubation time (days) | | | |
|---|---|---|---|---|---|
| | | 3 | 4 | 5 | 6 |
| | | Percent infection[a] | | | |
| Grapefruit | NRRL Y-18314 | 3 | 3 | 8 | 9 |
| (72) | Control | 30 | 56 | 78 | 86 |
| Lemon | NRRL Y-18314 | 12 | 17 | 18 | 18 |
| (30) | Control | 75 | 77 | 77 | 77 |

[a]Number of inoculation sites per treatment is indicated in parentheses under the cultivar's name.

As shown in Table I, isolate NRRL Y-18314, was highly effective in inhibiting *Penicillium digitatum* decay on citrus fruit in all cultivars tested. The effectiveness of NRRL Y-18314 varied depending upon the sensitivity of the cultivar to the decay. When compared to its effectiveness on grapefruit, isolate NRRL Y-18314 was more effective on pummelo fruit but less effective on temple, lemon, orange, or kumquat fruits.

Table II shows that isolate NRRL Y-18314 was effective in inhibiting *Penicillium italicum* decay on grapefruit, oranges and other citrus fruit cultivars. As in the case of *Penicillium digitatum*, NRRL Y-18314 more effectively controlled *Penicillium italicum* in grapefruits than in oranges. NRRL Y-18314 was also effective in inhibiting the development of *Geotrichum candidum* in citrus fruits. However, as shown in Table III, *Geotri-* chum candidum was controlled to a lesser extent than the Penicillia decays, particularly in lemons.

EXAMPLE II

The ability of NRRLY-18314 to inhibit Rhizopus rot development in grapes was demonstrated.

A biologically pure culture of NRRL Y-18314 was isolated and purified as described in Example I.

NRRLY-18314 was incubated in 100 ml of NYDB in 250 ml Erlenmeyer flasks on a rotary shaker (100 rpm) at 28° C. for 48 hours. Freshly harvested grapes of the Perlette and Thompson Seedless cultivars were dipped momentarily in a suspension of the organism in NYDB. The berries were treated as whole clusters with non-injured berries, as injured berries which had been removed from the stems by pulling and thereby causing a wound, or as injured single berries wounded by piercing non-injured berries with a needle. Control berries were dipped in sterile NYDB only.

One to two hours after t he berries had been dipped in the suspension, the berries were dried and thereafter inoculated by dipping in an aqueous suspension containing spores of the targeted pathogen at a concentration of $1 \times 10^4$ spores/ml. Alternatively, the berries were inoculated by placing a single decayed berry in the center of a group of non-injured berries, i.e. "nesting". The treated berries were placed in polyethylene-covered cartons and held at room temperature for 5 days. Whole treated clusters were placed directly in commercial shipping cartons.

Decay incidence was determined by counting the number of infected berries. Each treatment in each experiment consisted of at least three replicates of 20 berries or four replicates of five intact clusters placed in half of a shipping carton.

The results were analyzed and are shown in FIG. 1.

As shown in FIG. 1, NRRLY-18314 was effective in reducing Rhizopus rot in both injured and non-injured grape berries. Reduction of decay was most pronounced in those berries that were not injured prior to inoculation and in those inoculated by nesting.

EXAMPLE III

The effectiveness of isolate NRRLY-18314 to inhibit *Botrytis cinerea* and *Penicillium expansum* rot was tested on apples.

Golden Delicious apples were washed with 2% sodium hypochlorite to surface sterilize the fruit. After air drying, the apples were placed on styrofoam trays in plastic trays with lids. Water (100 ml) was added to the bottom of each plastic tray in order to maintain high humidity. The apples were wounded using a needle. Wound size was 4 mm wide by 5 mm deep. Three-day old shake cultures of NRRL Y-18314 growing on NYDB at a $1 \times 10^9$ CFU/ml concentration was added to the wounds, 50 microliters/wound. Treated apple wounds were allowed to air dry. Controls were inoculated with water only. There were 10 replicates per treatment each consisting of a single wound per fruit. Thereafter, an aqueous suspension of *Botrytis cinerea* or *Penicillium expansum* spores, $1 \times 10^4$ spores/ml, were added to the wounds, 20 microliters/wound.

Figure 2:
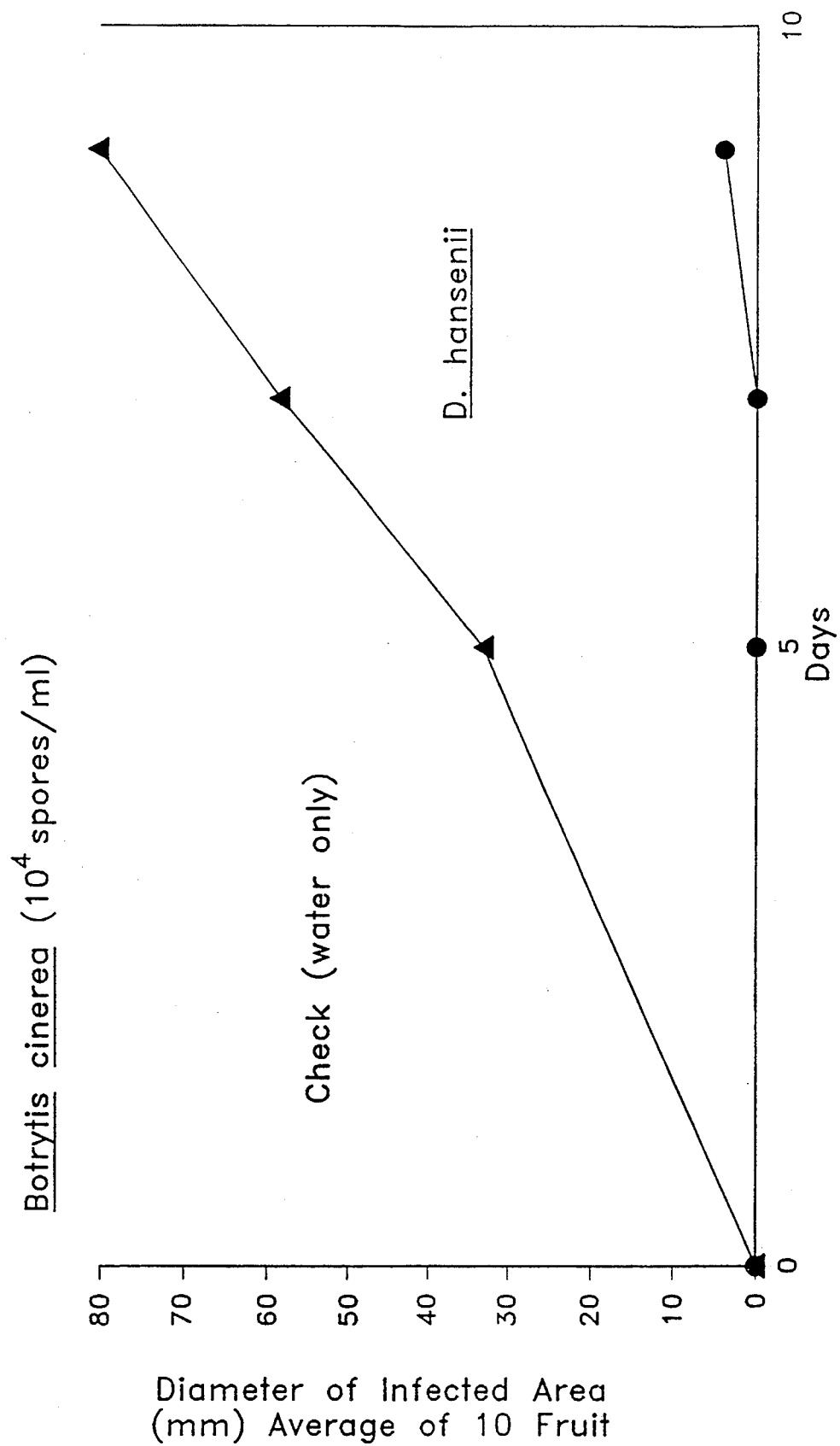
FIG. 2 is a line graph of diameter of area (ram) infected with *Botrytis cinerea* on apples rs. time (days), for: (1) control samples treated with water only, and; (2) samples treated with NRRL-Y-18314.
Figure 3:
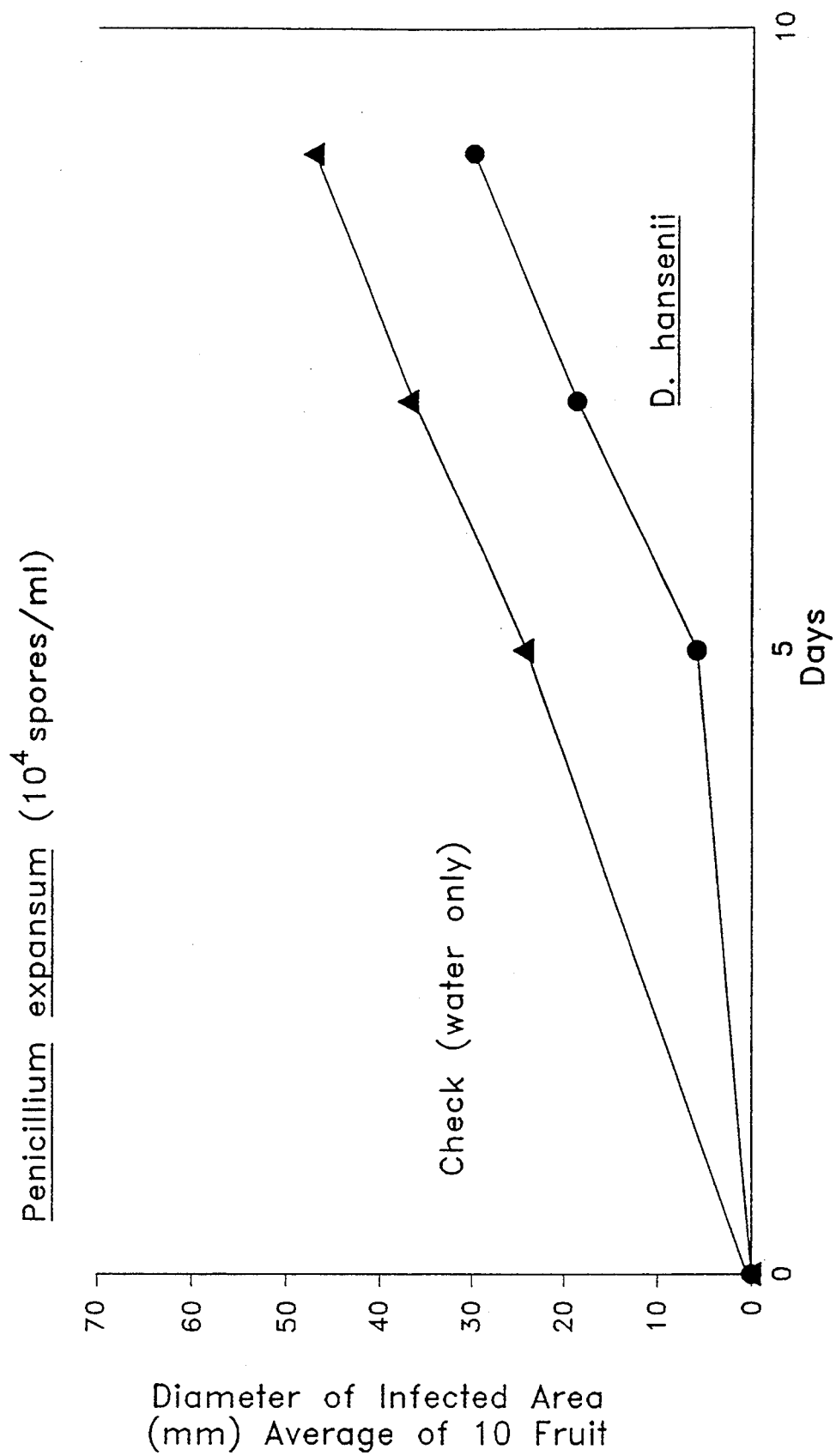
FIG. 3 is a line graph of diameter of area (ram) infected with *Penicillium expansum* on apples vs. time (days) for: (1) control samples treated with water only, and; (2) samples treated with NRRL-Y-183 14.

Measurements of infected areas were taken 5, 7, and 9 days after inoculation. Results were analyzed and are shown in FIGS. 2 and 3.

NRRL Y-18314 effectively controlled both *Borytis cinerea* and *Penicillium expansum* rots in apples. As shown in FIG. 2, total protection against *Botrytis cinerea* occurred in treated apples up to about 7 days after inoculation, with only small lesion development after nine days. Protection against *Penicillium expansum* was to a lesser extent than against *Botrytis cinerea*. Nevertheless, FIG. 3 clearly shows that apples treated with NRRLY-18314 had a significant decrease in the development of *Penicillium expansum* when compared to the untreated controls.

EXAMPLE IV

The effectiveness of NRRL Y-18314, to inhibit *Penicillium digitatum* on grapefruit was compared to the effectiveness of eight previously identified isolates of *D. hansenii.*

The eight isolates were obtained from the American Type Culture Collection, hereinafter referred to as "ATCC" located at 12301 Parklawn Drive, Rockville, Md. 20252, USA. Identification of the isolates tested were as follows: ATCC 18538, ATCC 20220, ATCC 36239, ATCC 34022, ATCC 36239, ATCC 9367, ATCC 36767, and ATCC 18107.

Each isolate tested was incubated in NYDB liquid medium at 28° C. for 48 hours. Following centrifugation, the resulting pellets were washed twice with water and thereafter suspended in water. Concentrations of the aqueous suspensions ranged from $1.3 \times 10^7$ to $1.3 \times 10^9$ CFU/ml.

Figure 4:
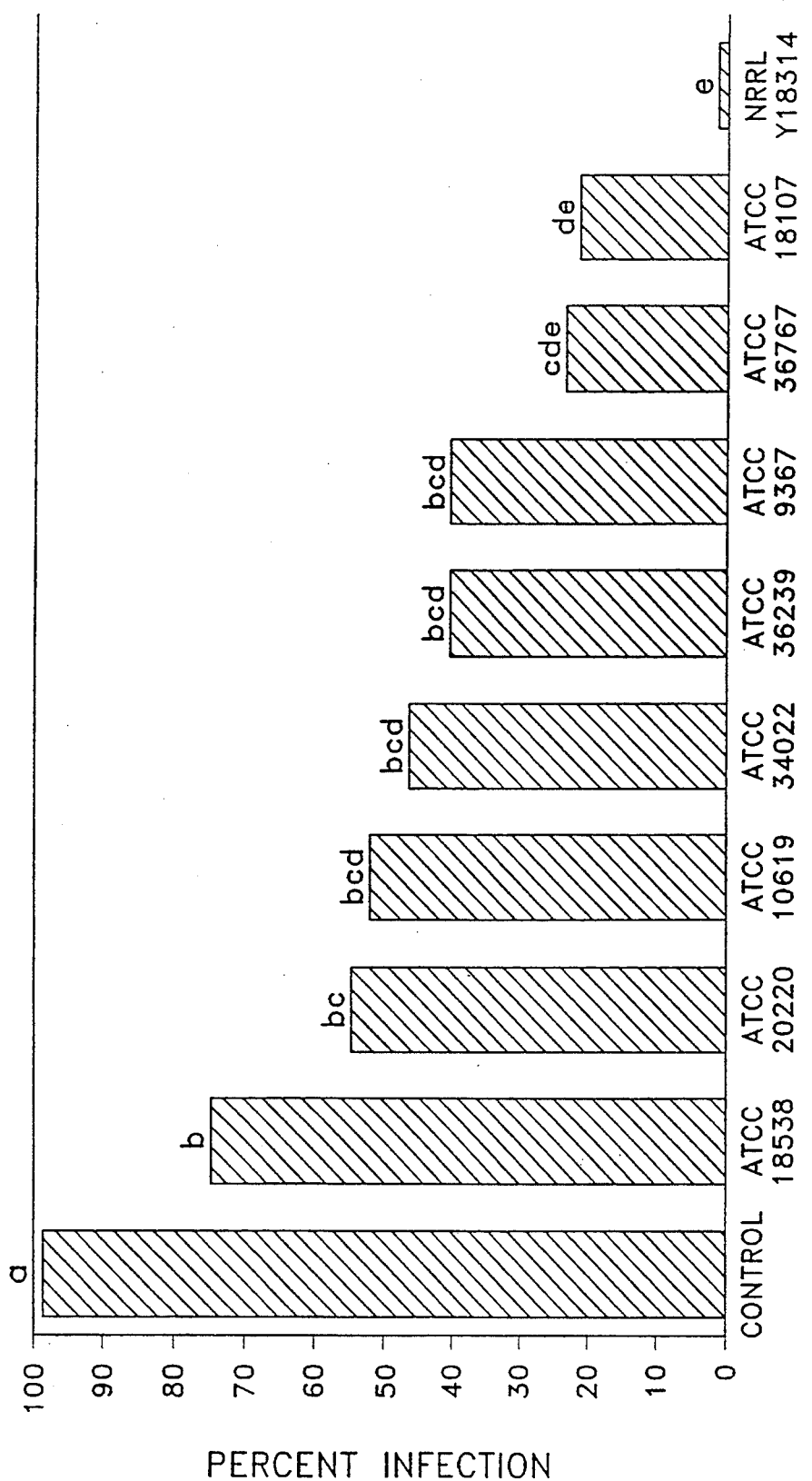
FIG. 4 is a bar graph of percent infection showing relative effectiveness of yeast isolates to inhibit *Penicillium digitatum* decay on grapefruit.

The surface of the grapefruit was sterilized with 95% ethanol and placed on moist paper in $50 \times 100 \times 15$ cm plastic trays, 24 fruits per tray. Thereafter, the surface of the fruit was wounded using a needle. Two to four conical wounds, 3 mm deep, were cut in the fruit peel. An aqueous suspension of each isolate was brushed onto the surface of a wound. Each isolate was tested on 48 sites of inoculations. One to two hours later, an aqueous suspension of *Penicillium digitatum*, $1 \times 10^5$ spores/ml, was added to the wounds, 20 microliters/wound. Controls were inoculated with water only. The percent of fruit infection was recorded 7 days after inoculation. The data was analyzed by analysis of variance and means were separated by Duncan's New Multiple Range Test. Different letters are significant at a 1% level. The results are recorded in FIG. 4.

NRRL Y-18314 clearly exhibited superior control of *Penicillium digitatum* when compared to prior identified isolates of *D. hansenii.* After seven days of inoculation, total protection occurred in grapefruits inoculated with NRRL Y-18314 while as much as 25 to 65% infection occurred in fruits inoculated with isolates obtained from the ATCC.

EXAMPLE V

Figure 5A:
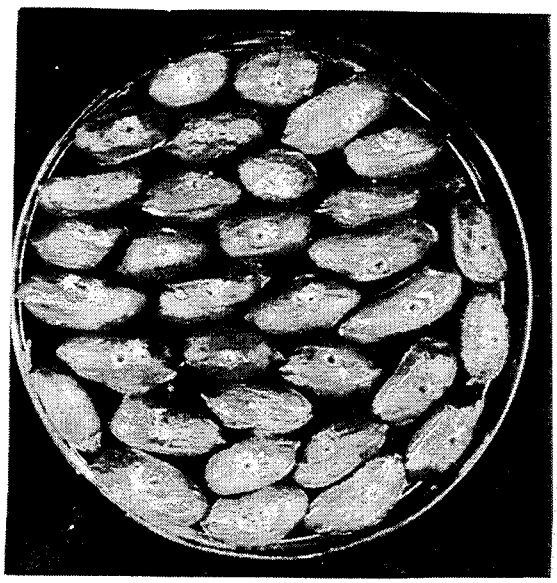
FIG. 5A is a photograph of peanuts treated with both *Aspergillus flavus* and NRRL-Y-18314 in accordance with Example V.
Figure 5B:
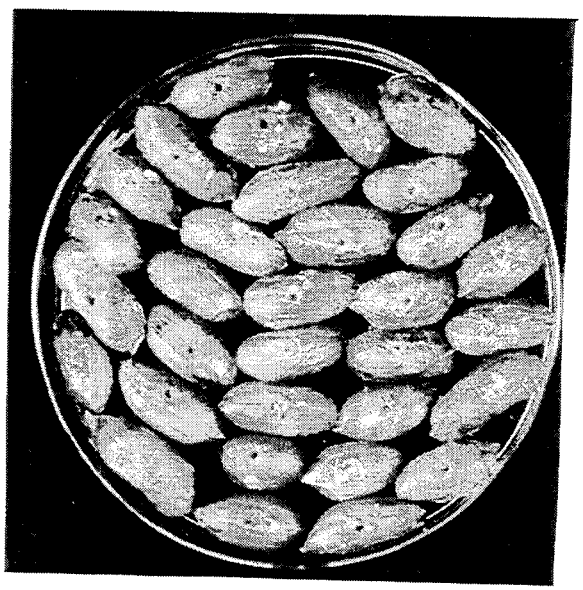
FIG. 5B is a photograph of peanuts treated with only *Aspergillus flavus*, according to Example V.

The purpose of this example is to show the effectiveness of isolate NRRL-Y-18314 at inhibiting *Aspergillus flavus* on peanuts. The peanuts were prepared in the following manner. A wound was cut in the surface of each nut. The NRRL Y-18314 was applied as described in Example 1. Similarly, the *Aspergillus flavus* was applied as described for the pathogen in Example 1. The treated nuts were incubated 14 days at 26° C. FIG. 5A is photograph of the peanuts treated with both *Aspergillus flavus* and NRRL-Y-18314, and FIG. 5B is a photograph of peanuts treated only with .Aspergillus flavus. As shown in these photographs, the results clearly show the inhibition by the yeast of the pathogen growth: FIG. 5A shows only 11 (33%) Of the wounds on which the pathogen grew (low to medium growth) compared with FIG. 5B which shows extensive pathogen growth on 100% of the wounds.

EXAMPLE VI

Figure 6A:
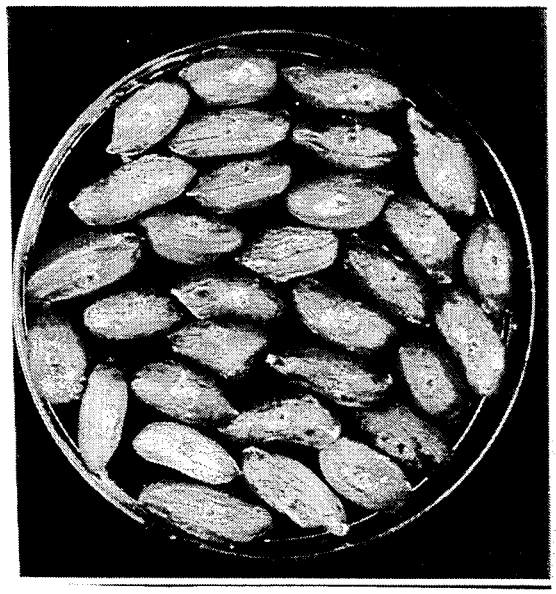
FIG. 6A is a photograph of peanuts treated with both *Aspergillus niger* and NRRL-Y-18314 as referred to in Example VI.
Figure 6B:
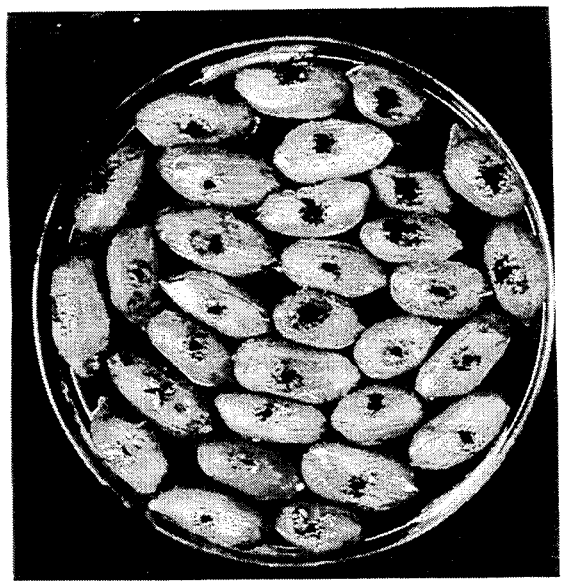
FIG. 6B is a photograph of peanuts treated with only *Aspergillus niger* according to the process described in Example VI.

The purpose of this example is to show the effectiveness of isolate NRRL-Y-18314 at inhibiting *Aspergillus niger* on peanuts. The peanuts were prepared in the following manner. A wound was cut in the surface of each nut. The NRRLY-18314 was applied as described in Example 1. Similarly, the *Aspergillus niger* was applied as described for the pathogen in Example 1. The treated nuts were incubated 14 days at 26° C. FIG. 6A is a photograph of the peanuts treated with both *Aspergillus niger* and NRRL-Y-18314, and FIG. 6B is a photograph of peanuts treated only with *Aspergillus niger*. As shown in these photographs, the results show complete inhibition of the pathogen growth in the yeast-treated nuts (FIG. 6A) compared with 100% infection in the non-treated control (FIG. 6B).

EXAMPLE VII

Twenty-five milliliters of a 48-hour-old NRRL-Y-18314 culture was centrifuged. The resulting pellet was resuspended in 10 ml. of each of the following: (A) a wax including a paraffin mineral oil base obtained from Durant-Wayland Inc., La Grange, Ga.; (B) Fresh Wax; (C) Stayfresh water based wax from FMC Corporation, Woodstock, Va.; (D) "Fresh Wax 58P" including a paraffin mineral oil base, referred to herein above. Initial dilution counts (of CFU/ml) were made in each wax (i.e. initial, time zero counts). Dilutions were carried out at the time intervals indicated in Table IV (except as noted in said table), by mixing: (a) 0.1 milliliter of each mixture of wax and culture, with: (b) 0.9 milliliter of the respective wax. The resultant mixtures were then plated on yeast malt agar plates. The plates were maintained at about 20° to 25° C. Results are shown in Table IV. Entries in Table IV are all in colony forming units per milliliter.

TABLE IV

| | Durand-Wayland | Fresh Mark | Stayfresh | Fresh Wax 58P |
|---|---|---|---|---|
| Initially (Time Zero) | $1 \times 10^5$ | $1.0 \times 10^7$ | $8.9 \times 10^8$ | $1.0 \times 10^5$ |
| 19 Days | $2.5 \times 10^6$ | $2.0 \times 10^5$ | $2.9 \times 10^6$ | less than $1.0 \times 10^5$ |
| 35 Days | $2.7 \times 10^6$ | $1.4 \times 10^6$ | $9.0 \times 10^4$ | $1.9 \times 10^5$ |
| 46 Days | $5.9 \times 10^6$ | $8.4 \times 10^5$ | $3.0 \times 10^4$ | $1.5 \times 10^5$ |
| 60 Days | $1.1 \times 10^7$ | $2.3 \times 10^6$ | less than $1.0 \times 10^4$ | $4.9 \times 10^6$ |
| 76 Days | $3.0 \times 10^6$ | $4.9 \times 10^6$ | less than $1.0 \times 10^4$ | $1.5 \times 10^6$ |
| 258 Days | NT* | TNTC** | NT | TNTC |
| 342 Days | NT | TNTC | NT | TNTC |

**TNTC stands for too numerous to count.
*NT stands for not tested, i.e. dilution plates were not made.

This example clearly indicates the surprisingly and unexpectedly high viability of NRRL-Y-18314 in commercially available waxes at room temperature, even for extended periods of time.

EXAMPLE VIII

The purpose of this example is to show that either freeze dried cells or whole cells of NRRL-Y-18314 can remain viable in a commercially available wax (i.e. Fresh Mark Wax) for long periods of time. Freeze dried cells were frozen in liquid nitrogen and placed on a lyphilyzer for 48 hours and mixed with the wax, (4 volumes of wax to one volume of freeze dried cells). Whole cells were centrifuged into a pellet at 5000 RCF and resuspended in the wax. (4 volumes of wax to one volume of whole cell pellet). The results are shown in Table V. Entries in Table V are all in colony forming units (i.e. CFU) per milliliter.

TABLE V

| | Freeze Dried Cells of NRRL-Y-18314 | | Whole Cells of NRRL-Y-18314 | |
|---|---|---|---|---|
| Week | Stored at Room Temp. | Stored Under Refrigeration | Stored at Room Temp. | Stored Under Refrigeration |
| 1 | $3.52 \times 10^3$ | TNTC* | TNTC | TNTC |
| 2 | 350 | TNTC | TNTC | TNTC |
| 3 | 40 | TNTC | TNTC | TNTC |
| 5 | 0 | TNTC | TNTC | TNTC |
| 7 | 0 | TNTC | TNTC | TNTC |
| 9 | 0 | TNTC | TNTC | TNTC |
| 11 | 0 | TNTC | TNTC | TNTC |
| 13 | 20 | $9.88 \times 10^3$ | TNTC | TNTC |
| 16 | 0 | $5.8 \times 10^3$ | TNTC | TNTC |
| 19 | 20 | $6.28 \times 10^3$ | TNTC | TNTC |
| 24 | 10 | $5.54 \times 10^3$ | TNTC | TNTC |
| 37 | 0 | $1.83 \times 10^3$ | TNTC | TNTC |
| 57 | | | TNTC | TNTC |

*TNTC = too numerous to count, no count greater than $1 \times 10^4$ CFU/ml was made.

EXAMPLE IX

Five milliliters of a YM broth culture of NRRL-Y-18314 ($5.6 \times 10^8$ CFU/ml) were mixed with 5 milliliters of gum. Gum concentration of the 5 milliliter solutions ranged from 1–20% as indicated in Table VI. The culture and gum mixture was added to 40 cm$^3$ of either corn starch (25.7 g) or silica gel (27.1 g). This preparation was mixed and dried at 54° C. for 4 days and then ground in a mortar and pestle to a fine powder. The powder was then stored at 4° C. One gram of this powder was added to 10 milliliters of sterile water and mixed with a stirring bar for 20 minutes and dilution plating was done to determine NRRL-Y-18314 populations. The results are shown in Table VI in units of colony forming units per milliliter.

TABLE VI

| | 9 DAYS | 24 DAYS | 37 DAYS | 56 DAYS |
|---|---|---|---|---|
| CORN STARCH | | | | |
| Tragacanth 1% | less than $1.0 \times 10^5$ | less than $1.0 \times 10^4$ | | |
| Karaya 10% | $3.0 \times 10^5$ | $5.0 \times 10^4$ | $2.0 \times 10^4$ | $5.0 \times 10^4$ |
| Locust Bean 15% | less than $1.0 \times 10^5$ | $2.0 \times 10^4$ | $3.0 \times 10^4$ | $1.8 \times 10^5$ |
| Xanthan 20% | $8.0 \times 10^5$ | $7.3 \times 10^5$ | $3.0 \times 10^5$ | $5.9 \times 10^5$ |
| SILICA GEL | | | | |
| Tragacanth 1% | less than $1.0 \times 10^5$ | less than $1.0 \times 10^4$ | | |
| Karaya 10% | $2.0 \times 10^5$ | $1.0 \times 10^4$ | less than $1.0 \times 10^4$ | |
| Locust Bean 15% | less than $1.0 \times 10^5$ | less than $1.0 \times 10^4$ | | |
| Xanthan 20% | $1.0 \times 10^5$ | $1.1 \times 10^5$ | $1.0 \times 10^4$ | |

These results clearly show that the NRRL-Y-18314 remained viable for an extended period of time in any of a variety of gums combined with either corn starch or silica gel.

EXAMPLE X

The same procedures were followed as in Example IX except talc (28 grams) was used instead of either the corn starch or silica gel. The results are shown in Table VII in units of colony forming units per milliliter.

TABLE VII

|                 | 5 DAYS              | 19 DAYS             | 33 DAYS                   | 48 DAYS             | 61 DAYS             | 80 DAYS             | 88 DAY          |
|-----------------|---------------------|---------------------|---------------------------|---------------------|---------------------|---------------------|-----------------|
| Methylcellulose | | | | | | | |
| 1%              | $6.4 \times 10^6$   | $5.2 \times 10^6$   | $3.0 \times 10^5$         | $8.6 \times 10^5$   | $6.8 \times 10^5$   | $4.3 \times 10^5$   |                 |
| 5%              | $6.1 \times 10^6$   | $6.8 \times 10^6$   |                           |                     |                     |                     |                 |
| Guar        | | | | | | | |
| 1%              | $3.1 \times 10^6$   | $3.8 \times 10^6$   | less than $1.0 \times 10^5$ | $8.0 \times 10^4$ | $2.3 \times 10^5$   | $8.0 \times 10^4$   |                 |
| 5%              | $6.0 \times 10^5$   | $1.1 \times 10^6$   |                           |                     |                     |                     |                 |
| 10%             | $1.3 \times 10^6$   | $2.0 \times 10^6$   |                           |                     |                     |                     |                 |
| Xanthan     | | | | | | | |
| 1%              | $4.3 \times 10^6$   | $7.2 \times 10^6$   |                           |                     |                     |                     |                 |
| 5%              | $1.3 \times 10^7$   | $2.1 \times 10^7$   |                           |                     |                     |                     |                 |
| 10%             | $2.7 \times 10^7$   | $2.8 \times 10^7$   | $1.8 \times 10^6$         |                     |                     |                     |                 |
| 20%             | $3.6 \times 10^7$   | $3.2 \times 10^7$   | $3.6 \times 10^6$         | $4.1 \times 10^6$   | $6.7 \times 10^6$   | $2.6 \times 10^6$   |                 |
| Locust Bean | | | | | | | |
| 1%              | $4.1 \times 10^6$   | $3.8 \times 10^6$   |                           |                     |                     |                     |                 |
| 5%              | $1.0 \times 10^7$   | $6.2 \times 10^6$   |                           |                     |                     |                     |                 |
| 10%             | $5.8 \times 10^6$   | $7.4 \times 10^6$   | $5.0 \times 10^5$         |                     |                     |                     |                 |
| 15%             | $1.1 \times 10^7$   | $1.2 \times 10^7$   | $8.0 \times 10^5$         | $4.9 \times 10^5$   | $6.3 \times 10^5$   | $1.3 \times 10^6$   |                 |
| Karaya      | | | | | | | |
| 1%              | $1.6 \times 10^7$   | $1.1 \times 10^7$   |                           |                     |                     |                     |                 |
| 5%              | $1.2 \times 10^7$   | $1.0 \times 10^7$   |                           |                     |                     |                     |                 |
| 10%             | $5.5 \times 10^7$   | $2.2 \times 10^7$   | $1.7 \times 10^6$         | $1.2 \times 10^6$   | $2.9 \times 10^6$   | $1.8 \times 10^6$   |                 |
| 25%             | $1.3 \times 10^7$   | $1.9 \times 10^7$   | $2.2 \times 10^6$         |                     |                     |                     | $1.8 \times 10^6$ |
| Tragacanth  | | | | | | | |
| 1%              | $8.0 \times 10^6$   | $1.3 \times 10^7$   | $1.4 \times 10^6$         | $5.4 \times 10^5$   | $9.1 \times 10^5$   | $7.6 \times 10^5$   |                 |
| 5%              | $5.1 \times 10^6$   | $9.6 \times 10^6$   | $8.0 \times 10^5$         |                     |                     |                     |                 |
| 10%             | $1.9 \times 10^6$   | $7.8 \times 10^6$   |                           |                     |                     |                     |                 |
| 25%             | $2.4 \times 10^6$   | $6.2 \times 10^6$   |                           |                     |                     |                     |                 |

These results clearly show that the NRRL-Y-18314 remained viable for extended periods of time in various combinations of talc and gum.

EXAMPLE XI

The purpose of this example is to show that $CaCl_2$ and $CaCO_3$ improve biocontrol, are more effective at improving biocontrol than other inorganic salts, and illustrate surprising and unexpected synergistic results. Golden delicious apples were artificially wounded to a depth of 3 mm using a needle. Each of a first portion of the apples was treated with 50 microliter aliquots of an aqueous solution consisting of NRRL Y-18314 in sterile distilled water at a concentration of $10^7$ CFU/ml with each of the salts listed in Table VIII at a concentration of 2 grams/100 ml (with the exception of $FeSO_4$ which was utilized at a 5 millimolar concentration). A second portion of the apples was treated with a 50 microliter aqueous solution of each of the salts listed in Table VIII at a concentration of 2 grams/100 ml (with the exception of $FeSO_4$ which was utilized in a concentration of 5 millimolar). Also a control was run using only sterile distilled water. Two hours after application of the above solutions, each of the apples was challenged with 20 microliters of a $10^5$ spore/ml suspension of *Botrytis cinerea*. The average percent fruit infection of four trials (8 to 10 replicates per trial) was measured 10 days after inoculation with the *Botrytis cinerea*. The results are shown in Table VIII.

TABLE VIII

|                   | Percent Infection           | |
|-------------------|-----------------------------|-----------------------------|
| Inorganic Salt    | Salt Alone (No NRRL Y-18314) | Salt and NRRL Y-18314      |
| $CaCl_2$          | 95.0 ($\pm 5.0$)            | 3.3 ($\pm 3.3$)*            |
| $CaCO_3$          | 71.9 ($\pm 13.5$)           | 27.5 ($\pm 24.3$)*          |
| $FeSO_4$          | 87.5 ($\pm 12.5$)           | 57.5 ($\pm 21.0$)           |
| $KCl$             | 100.0 ($\pm 0.0$)           | 47.5 ($\pm 20.6$)*          |
| $MgCl_2$          | 100.0 ($\pm 0.0$)           | 61.3 ($\pm 17.4$)           |
| $MnCl_2$          | 100.0 ($\pm 0.0$)           | 97.5 ($\pm 2.5$)            |
| $NaCl$            | 100.0 ($\pm 0.0$)           | 71.6 ($\pm 15.7$)           |
| CONTROLS $H_2O$   | 100.0 ($\pm 0.0$)           | 59.5 ($\pm 14.4$)           |

Values in parentheses are standard errors of the mean. Asterisk indicates that means within a row are significantly ($P < 0.05$) different according to SAS GLM analysis of variance on arcsin square root-transformed data. It may be observed that none of the salts used alone provided statistically significant reduction of infection (i.e. none of the values for use of salt alone differ significantly from use of water alone i.e. 100% infection). Further the combination of NRRL Y-18314 and the calcium salts clearly provide synergistic infection reduction, as evidenced by the fact that $CaCl_2$ and $CaCO_3$ provided approximately 5% and approximately 18% infection reduction when used alone and the NRRL Y-18314 provided approximately 40% infection reduction when used alone. Therefore it may have been presumed that the additive effect would have been 45% or 58% respectively. However, in actuality, the combination of $CaCl_2$ with NRRL Y-18314 provided more than twice the expected value of 45% i.e. about 96.7%; and the combination of $CaCO_3$ with NRRL Y-18314 provided 72.5% which is significantly higher than the expected value of 58%.

EXAMPLE XII

The purpose of this example is to show that calcium salts provide improved biocontrol with a variety of yeast strains from different species. Golden Delicious apples were wounded in accordance with the previous example. The apples were then treated with 50 microliters of a $10^8$ CFU/ml suspension of the respective yeasts in sterile distilled water, with or without 2 grams/100 ml of $CaCl_2$ as referred to in Table IX. Two hours later the apples were challenged with 20 microliters of a suspension of $10^4$ spores/milliliters of Botrytis cinerea. Seven days after inoculation percent infection was observed. Results are shown in Table IX.

TABLE IX

| Yeast Strain | $CaCl_2$ | Average Percent Infection |
| --- | --- | --- |
| NRRL-Y-18527 | YES | 6.7 (±6.7)* |
| NRRL-Y-18527 | NO | 41.7 (±18.8) |
| NRRL-Y-18314 | YES | 0.0 (±0.0)* |
| NRRL-Y-18314 | NO | 26.7 (±6.7) |
| NONE | YES | 100.0 (±0.0) |
| NONE | NO | 100.0 (±0.0) |

The above entries are the average of 3 trials per treatment. Values in parentheses are standard errors of the mean. Asterisk indicates that fruit rot in yeast treatments with calcium chloride is significantly ($P \leq 0.05$) less than that of fruit treated with yeast alone. It my be observed that significant infection reduction was achieved using either of the yeast, and that further infection reduction was achieved using the combination of $CaCl_2$ with each yeast.

EXAMPLE XIII

The purpose of this example is to demonstrate the effectiveness of NRRLY-18314 and combinations thereof with $CaCl_2$ for controlling Penicillium rot. Golden delicious apples were artificially wounded in accordance with Example XI. The wounded apples were then treated with a 50 microliter suspension of NRRLY-18314 in sterile distilled water, with or without $CaCl_2$ (concentration of 2 gram/100 ml) as noted in Table X. Two hours later the apples were challenged with 20 microliters of a spore suspension of Penicillium expansum at the concentrations referred to in Table X. Seven days after inoculation lesion diameter was observed. Results are shown in Table X.

TABLE X

| Presence of $CaCl_2$ | NRRL-Y-18314 Concentration (CFU/ml) | Penicillium spore Concentration (spores/ml) | Average Lesion Diameter (mm) | Standard Error |
| --- | --- | --- | --- | --- |
| NO | $10^7$ | $10^3$ | 32.4 | 8.4 |
| NO | $10^7$ | $10^4$ | 49.8 | 2.1 |
| NO | $10^7$ | $10^5$ | 40.8 | 6.1 |
| NO | $10^8$ | $10^3$ | 18.4 | 7.9 |
| NO | $10^8$ | $10^4$ | 35.2 | 2.1 |
| NO | $10^8$ | $10^5$ | 36.2 | 9.2 |
| YES | $10^7$ | $10^3$ | 14.4 | 7.4 |
| YES | $10^7$ | $10^4$ | 9.0 | 6.3 |
| YES | $10^7$ | $10^5$ | 15.2 | 9.3 |
| YES | $10^8$ | $10^3$ | 7.6 | 5.3 |
| YES | $10^8$ | $10^4$ | 17.4 | 5.8 |
| YES | $10^8$ | $10^5$ | 19.2 | 6.7 |
| YES | 0 | $10^3$ | 40.4 | 1.9 |
| YES | 0 | $10^4$ | 45.2 | 1.6 |
| YES | 0 | $10^5$ | 47.0 | 1.6 |
| NO | 0 | $10^3$ | 47.2 | 2.3 |

The entries of Table X are the average of 5 replicates per treatment. It maybe observed from the table that the isolate NRRLY-18314, applied in the absence of $CaCl_2$, did not facilitate significant reduction of decay (greater than 50%) inmost treatments, as compared to the water control and $CaCl_2$ treatments without NRRLY-18314. However, when NRRLY-18314 was applied with $CaCl_2$ decay was reduced greater than 50% at all yeast concentrations and at all Penicillium spore concentrations tested.

EXAMPLE XIV

The purpose of this example is to illustrate the synergistic effects of combinations of various concentrations of $CaCl_2$ and microorganisms of the present invention. Grapefruit was wounded as in Example I. The wounded grapefruit were then treated with 50 microliter aliquotes of the constituents identified in Tables XI and XII in sterile distilled water. Two hours later the apples were challenged with 20 microliters of a $10^4$ spore/milliliter suspension of Penicillium digitatum. The grapefruit were incubated for 5 days at 24° C. before observations were taken. Results of average percent fruit rot were as follows (data is the average of 2–3 trials per treatment):

TABLE XI

| | FOR STRAIN NRRL-Y-18314 | | | |
| --- | --- | --- | --- | --- |
| | Average Percent Fruit Rot | | | |
| $CaCl_2$ | NRRL-Y-18314 Concentration (cfu/ml) | | | |
| Concentration | 0 | $10^6$ | $10^7$ | $10^8$ |
| 0% | 59.5 | 31.5 | 10.5 | 0 |
| 1% | 39.0 | 22.8 | 1.5 | NT* |
| 2% | 22.8 | 7.5 | 1.5 | NT |

*NT stands for "not tested".

TABLE XII

| | FOR STRAIN NRRL-Y-18313 | | | |
| --- | --- | --- | --- | --- |
| | Average Percent Fruit Rot | | | |
| $CaCl_2$ | NRRL-Y-18313 Concentration (cfu/ml) | | | |
| Concentration | 0 | $10^6$ | $10^7$ | $10^8$ |
| 0% | 91.7 | 69.0 | 23.3 | 6.5 |
| 1% | 63.0 | 3.0 | 6.0 | 1.5 |
| 2% | 33.0 | 7.3 | 7.3 | 14.3 |

EXAMPLE XV

The purpose of this example is to show that yeast cells rather than the yeast culture broth provide biocontrol, and that washed yeast cells provide improved biocontrol over that achieved with the yeast cells and culture broth. Peaches were artificially wounded and then treated with 50 microliters of washed yeast cells prepared by pelleting yeast cells from culture broth by centrifuging at 5,000 relative centrifugal force (RCF), the yeast cells were resuspended in sterile distilled water and repelleted by centrifugation as before and then resuspended with concentration adjustment in either water or culture broth to provide concentrations as specified in Table 13. A portion of the peaches were treated with only culture broth (without yeast cells). Two hours later the peaches were inoculated with 20 microliters of a $10^4$ spores/ml suspension of Rhizopus stolonifer. Average percent infection was observed 4 days later. The results are as follows (each value is the average of two to five trials):

TABLE XIII

AVERAGE PERCENT INFECTION

| Yeast Strain | Washed Yeast Cells (cfu/ml) | | | Washed Yeast Cells Resuspended in Culture Broth | | Culture Broth (without Yeast Cells) |
|---|---|---|---|---|---|---|
| | $10^9$ | $10^8$ | $10^7$ | $10^9$ | $10^8$ | |
| NRRL-Y-18527 | 10.0 (±7.1) | 15.0 (±8.2) | 57.0 (±21.6) | 32.5 (±7.5) | 75.0 (±25.0) | 100.0 (±0.0) |
| NRRL-Y-18314 | 2.5 (±2.5) | 35.0 (±11.5) | 90.0 (±10.0) | 30.0 (±20.0) | 87.5 (±12.5) | 100.0 (±0.0) |
| NRRL-Y-18313 | 3.3 (±3.3) | 34.4 (±14.1) | 87.5 (±12.5) | 52.5 (±22.5) | 100.0 (±0.0) | 100.0 (±0.0) |
| *Zygosaccharomyces rouxii* (ATTC #10682) | 40.0 (±20.0) | 63.3 (±27.3) | 76.7 (±23.3) | 75.0 (±25.0) | 100.0 (±0.0) | 100.0 (±0.0) |
| *Zygosaccharomyces rouxii* (ATTC #34517) | 49.7 (±20.2) | 76.3 (±13.2) | 96.7 (±3.3) | 80.0 (±0.0) | 100.0 (±0.0) | 100.0 (±0.0) |

EXAMPLE XVI

Single Thompson seedless grapes were wounded by pulling from stems. The grapes were then dipped in a suspension of the yeasts specified in Table XIV at concentration of $10^8$ to $10^9$ cfu/ml and incubated at 22° C. At 5 and 6 days the percent fruit rot by naturally occurring organisms (e.g. *Aspergillus niger* and *Rhizopus stolonifer*) was as follows (data is for 3 replicates of 20 berries per fruit treatment);

TABLE XIV

| Fruit Treatment | Percent Fruit Rot | |
|---|---|---|
| | 5 DAYS | 6 DAYS |
| NRRL-Y-18527 | 5.0% | 13.0% |
| Y-18314 | 18.0% | 31.0% |
| Water | 90.0% | 100.0% |
| NYDB[1] | 50.0% | 92.0% |

[1]NYDB = sterile culture broth, nutrient yeast dextrose broth.

Fruit rot due to Rhizopus was not observed in grapes treated with any of the yeast treatments.

EXAMPLE XVII

Whole clusters of "Perlett" grapes were dipped in suspensions of the yeast antagonists specified in Table XV at concentrations of $10^8$ to $10^9$ cfu/ml. Two replicates of 6 fruit clusters were used for each treatment. Percent of naturally occurring fruit rot was observed after 7 days of storage at 20° C. The results were as follows:

TABLE XV

| Yeast Treatment | n | Percent Fruit Rot | | | |
|---|---|---|---|---|---|
| | | Aspergillus | Botrytis | Rhizopus | Total |
| NRRL-Y-18527 | 825 | 1.8% | 2.0% | 3.2% | 7.0% |
| NRRL-Y-18314 | 825 | 0.7% | 0.6% | 8.2% | 9.5% |
| Water | 890 | 1.4% | 3.0% | 16.2% | 20.6% | n = number of fruit per treatment.

It is understood that modifications and variations may be made to the foregoing disclosure without departing from the spirit and scope of the invention.

We claim:

1. A process for inhibiting plant pathogen development on an agricultural commodity comprising:
   applying to an agricultural commodity a composition comprising at least one microorganism, which is an antagonist against plant pathogens but is not antibiotic, in an amount effective to inhibit plant pathogen development on said agricultural commodity, wherein said at least one microorganism is a yeast selected from the group consisting of *Pichia guilliermondii* and *Hanseniasporum uvarum*.

2. The process of claim 1 wherein said yeast is *Pichia guilliermondii*.

3. The process of claim 2, wherein said yeast is *Pichia guilliermondii* having the identifying characteristics of deposit NRRL Y-18313 or NRRL Y-18314, wherein said identifying characteristics are antagonism to plant pathogens but not antibiotic activity.

4. The process of claim 1, wherein said yeast is *Hanseniaspora uvarum*.

5. The process of claim 3 wherein said yeast is *Pichia guilliermondii* having the identifying characteristics of deposit NRRL Y-18313, wherein the identifying characteristics are antagonism to plant pathogens but not antibiotic activity.

6. The process of claim 3 wherein said yeast is *Pichia guilliermondii* having the identifying characteristics of deposit NRRL Y-18314, wherein the identifying characteristics are antagonism to plant pathogens but not antibiotic activity.

7. The process of claim 4 wherein said yeast is *Hanseniasporum uvarum* having the identifying characteristics of deposit NRRL Y-18527, wherein the identifying characteristics are antagonism to plant pathogens but not antibiotic activity.

8. The process of claim 1 wherein said composition additionally includes an additive selected from the group consisting of pesticides, preservatives, carriers, surfactants, wetting agents and mixtures thereof.

9. The process of claim 8 wherein said carrier is selected from the group consisting of a gel based carrier, a gum based carrier, a water based carrier, a wax based carrier, an oil based carrier, a talc based carrier, a starch based carrier and mixtures thereof.

10. The process of claim 1 wherein said composition comprising at least one microorganism is essentially free of other microorganisms.

11. The process of claim 1, wherein said plant pathogen is selected from the group consisting of *Penicillium italicum* Webruer, *Penicillium digitatum*, *Botrytis cinerea*, *Rhizopus stolonifer*, *Geotrichum candidum*, *Penicillium expansum*, *Alternaria alternata*, *Aspergillus flavus*, *Aspergillus niger*, *Rhizopus arrhizus*, *Gilbertella persicovia*, *Mucor* spp., *Pezicula malicorticas*, *Monilinia* spp. and bacterial pathogens.

12. The process of claim 1, wherein said agricultural commodity is selected from the group consisting of fruits, vegetables, cereals, grains, nuts, seeds and silage.

13. The process of claim 12 wherein said agricultural commodity is a fruit selected from the group consisting of a citrus fruit, grape, apple, pear, tomato, persimmon, strawberry, peach, apricot, cherry, papaya, raisin, prune, fig, dried apricot and date.

14. The process of claim 13 wherein said agricultural commodity is citrus fruit selected from the group consisting of grapefruit, orange, lemon, kumquat, lime and pummelo.

15. The process of claim 12 wherein said agricultural commodity is a nut selected from the group consisting of peanuts, almonds and pecans.

16. The process of claim 12 wherein said agricultural commodity is a grain selected from the group consisting of wheat, corn, sorghum, soybeans and barley.

17. The process of claim 1, wherein said step of applying includes dusting, injecting, rubbing, spraying or brushing said agricultural commodity with the composition containing said at least one microorganism.

18. The process of claim 1, wherein said step of applying includes dipping or rolling said agricultural commodity in the composition containing said at least one microorganism.

* * * * *

UNITED STATES PATENT AND TRADEMARK OFFICE
CERTIFICATE OF CORRECTION

PATENT NO. : 5,413,783
DATED : 5/9/95
INVENTOR(S) : McLaughlin, R., Wilson, C., and Chalutz, E.

It is certified that error appears in the above-identified patent and that said Letters Patent is hereby corrected as shown below:

Column 20,
Claim 11, Line 3, "Webruer" should be -- Wehmer --.

Signed and Sealed this

Eighth Day of August, 1995

Attest:

BRUCE LEHMAN

Attesting Officer

Commissioner of Patents and Trademarks